US011996645B2

(12) United States Patent
Loo et al.

(10) Patent No.: US 11,996,645 B2
(45) Date of Patent: May 28, 2024

(54) SEPARABLE HIGH DENSITY CONNECTORS FOR IMPLANTABLE DEVICE

(71) Applicant: Verily Life Sciences LLC, South San Francisco, CA (US)

(72) Inventors: Alexander Loo, Redwood City, CA (US); Cindy Au, Redwood City, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 54 days.

(21) Appl. No.: 17/764,490

(22) PCT Filed: Sep. 29, 2020

(86) PCT No.: PCT/US2020/053256
§ 371 (c)(1),
(2) Date: Mar. 28, 2022

(87) PCT Pub. No.: WO2021/067260
PCT Pub. Date: Apr. 8, 2021

(65) Prior Publication Data
US 2022/0368055 A1 Nov. 17, 2022

Related U.S. Application Data

(60) Provisional application No. 62/908,753, filed on Oct. 1, 2019.

(51) Int. Cl.
*H01R 13/26* (2006.01)
*A61N 1/36* (2006.01)
(Continued)

(52) U.S. Cl.
CPC ......... *H01R 13/26* (2013.01); *A61N 1/36125* (2013.01); *A61N 1/3752* (2013.01);
(Continued)

(58) Field of Classification Search
CPC .... H01R 13/26; H01R 24/58; H01R 2105/00; H01R 2107/00; H01R 2201/12; A61N 1/36125; A61N 1/3752
See application file for complete search history.

(56) References Cited

U.S. PATENT DOCUMENTS 7,244,150 B1 * 7/2007 Brase ................... A61N 1/0551
607/46
8,224,450 B2 * 7/2012 Brase ................... A61N 1/3754
607/37

(Continued)

FOREIGN PATENT DOCUMENTS

| WO | 2017214183 | 12/2017 |
| WO | 2018119424 | 6/2018 |
| WO | 2019073003 | 4/2019 |

OTHER PUBLICATIONS

Application No PCT/US2020/053256, International Search Report and Written Opinion, dated Jan. 14, 2021, 7 pages.

*Primary Examiner* — Alexander Gilman
(74) *Attorney, Agent, or Firm* — Kilpatrick Townsend & Stockton LLP

(57) ABSTRACT

The present disclosure relates to implantable neuromodulation devices and methods of fabrication, and in particular to a separable high density connectors for implantable neuromodulation devices. Particularly, aspects of the present disclosure are directed to a medical device comprising an electronics module and a header for connecting the electronics module to a lead assembly. The header includes: a housing that includes (i) a cavity having a central axis or plane and an internal surface, and (ii) an opening aligned with the central axis or plane of the cavity, an array of retractable contacts extending from the internal surface towards the central axis or plane of the cavity, and an array of connection terminals on the housing, where each connec- (Continued)

tion terminal of the array of connection terminals is: (i) electrically connected to the electronics module, and (ii) electrically connectable to a retractable contact of the array of retractable contacts.

12 Claims, 10 Drawing Sheets

(51) Int. Cl.
*A61N 1/375* (2006.01)
*H01R 24/58* (2011.01)
*H01R 105/00* (2006.01)
*H01R 107/00* (2006.01)

(52) U.S. Cl.
CPC .......... *H01R 24/58* (2013.01); *H01R 2105/00* (2013.01); *H01R 2107/00* (2013.01); *H01R 2201/12* (2013.01)

(56) References Cited

U.S. PATENT DOCUMENTS

| | | | |
|---|---|---|---|
| 9,409,032 B2 * | 8/2016 | Brase | A61N 1/3752 |
| 9,770,598 B2 * | 9/2017 | Malinowski | H01R 13/187 |
| 10,307,602 B2 * | 6/2019 | Leven | A61N 1/3752 |
| 10,342,983 B2 * | 7/2019 | Nageri | A61B 5/6868 |
| 10,396,485 B1 * | 8/2019 | Smoll | H01R 13/41 |
| 10,543,374 B2 * | 1/2020 | Nageri | A61N 1/3605 |
| 10,603,499 B2 * | 3/2020 | Lopez | A61N 1/0551 |
| 10,814,136 B2 * | 10/2020 | Malinowski | A61N 1/3752 |
| 11,395,923 B2 * | 7/2022 | Lu | H05K 1/118 |
| 11,511,127 B2 * | 11/2022 | Orinski | A61N 5/0622 |
| 2012/0264318 A1 * | 10/2012 | Ishikawa | G01R 1/06722 |
| | | | 439/221 |
| 2014/0335288 A1 * | 11/2014 | Hirayama | H01J 37/32577 |
| | | | 118/723 R |
| 2014/0371547 A1 * | 12/2014 | Gartenberg | A61B 5/4812 |
| | | | 600/595 |
| 2016/0158544 A1 * | 6/2016 | Guarraia | A61N 1/0551 |
| | | | 607/2 |
| 2017/0100580 A1 * | 4/2017 | Olson | A61N 1/0551 |
| 2017/0348522 A1 * | 12/2017 | Stoffregen | A61N 1/0534 |
| 2018/0028820 A1 * | 2/2018 | Nageri | A61N 1/37235 |
| 2018/0243570 A1 * | 8/2018 | Malinowski | A61N 1/3752 |
| 2018/0289971 A1 * | 10/2018 | Yeh | A61B 5/686 |
| 2018/0369606 A1 * | 12/2018 | Zhang | A61B 5/4836 |
| 2019/0058284 A1 * | 2/2019 | Joniak | H01R 13/645 |
| 2019/0209849 A1 * | 7/2019 | Hershey | A61N 1/36062 |

* cited by examiner

SEPARABLE HIGH DENSITY CONNECTORS FOR IMPLANTABLE DEVICE

CROSS REFERENCE TO RELATED APPLICATIONS

This international application claims priority to U.S. Patent Application No. 62/908,753, filed on Oct. 1, 2019, the disclosure of which is herein incorporated by reference in its entirety for all purposes.

FIELD

The present disclosure relates to implantable neuromodulation devices and methods of fabrication, and in particular to a separable high density connectors for implantable neuromodulation devices.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis, epilepsy, obesity or depression; gastric and colonic stimulation for gastrointestinal disorders such as dysmotility or obesity; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant comprising a neurostimulator having electronics connected to a lead assembly that delivers electrical pulses to electrodes interfaced with nerves or nerve bundles via an electrode assembly. The lead assembly is typically formed of a conductive material and takes the form of an insulated wire (e.g., a dedicated channel) connected to the electrodes via a first connector on one end (e.g., a distal end) and the electronics of the neurostimulator via a second connector on another end (e.g., a proximal end). In some instances (e.g., deep implants), the lead assembly comprises additional conductors and connectors such as extension wires or a cable connected via connectors between the electrodes and the electronics of the neurostimulator.

Conventional neuromodulation devices include between four and sixteen electrodes, and thus typically include four to sixteen channels or wires connected respectively to the electrodes at the distal end and the electronics of the neurostimulator at the proximal end. However, there is a need for high density neural interfaces that include greater than sixteen electrodes to interface with larger tissue volumes, to recruit smaller populations of neurons for recording, or to provide more targeted therapy by tailoring the electrical stimulation parameters and activated tissue volume. Increasing the density or number of electrodes can increase the number of channels or wires needed to connect the electrodes and the electronics of the neurostimulator. In order to implement high channel or wire counts, there is a need for reliable electrical connections that can maintain contact and electrical isolation in a subject body (e.g., a patient body) for many years. Typically, a lead assembly containing a high channel or wire count needs to be permanently connected to the electronics. However, this is not ideal because the electronics need to be replaced every few years to upgrade them or to replace batteries, and surgeons have a strong preference not to remove the lead assembly from the neural tissue due to the risk to the patient. Therefore, there is a need for reliable and non-permanent connectors for lead assemblies having high density neural interfaces.

BRIEF SUMMARY

In various embodiments, a medical device is provided comprising: an electronics module; and a header for connecting to the electronics module to a lead assembly, the header comprising: a housing comprising (i) a cavity having a hollow portion defined by at least an internal surface, and (ii) an opening in communication with the hollow portion; an array of retractable contacts extending from the internal surface into the hollow portion, where the array of retractable contacts are arranged in one or more rows; and an array of connection terminals on the housing, where each connection terminal of the array of connection terminals is: (i) electrically connected to the electronics module, and (i) electrically connectable to a retractable contact of the array of retractable contacts.

In various embodiments, a medical device is provided comprising: an electronics module; and a header for connecting to the electronics module to a lead assembly. The header comprises: a housing comprising (i) a cavity having a central axis or plane and an internal surface, and (ii) an opening aligned with the central axis or plane of the cavity; an array of retractable contacts extending from the internal surface towards the central axis or plane of the cavity, where retractable contacts of the array of retractable contacts are arranged in a spatial configuration that spans one or more rows on the internal surface; and an array of connection terminals on the housing, where each connection terminal of the array of connection terminals is: (i) electrically connected to the electronics module, and (i) electrically connectable to a retractable contact of the array of retractable contacts.

In some embodiments, the retractable contacts comprise: a body with a columnar shape, a tip with a semi-circular shape, and an actuator for driving the retractable contacts in a direction perpendicular to the central axis or plane of the cavity.

In some embodiments, the retractable contacts comprise: a body with a spherical shape that allows the retractable contacts to rotate in a first direction parallel to the central axis or plane of the cavity, and an actuator for driving the retractable contacts in a second direction perpendicular to the central axis plane of the cavity.

In some embodiments, the actuator comprises: one or more set screws, a hydraulic bladder, a pneumatic bladder, a compression spring, a leaf spring, or a combination thereof.

In some embodiments, the cavity further includes a second internal surface located on a side of the cavity that is opposite of the first internal surface.

In various embodiments, a medical device is provided comprising: an electronics module; and a header for connecting the electronics module to a lead assembly. The header comprises: a housing comprising (i) a cavity having a central axis, a first internal surface, and a second internal surface located on a side of the cavity that is opposite of the first internal surface, and (ii) an opening aligned with the central axis or plane of the cavity; an array of retractable contacts extending from the first internal surface towards the central axis or plane of the cavity, where retractable contacts of the array of retractable contacts are arranged in a spatial configuration that spans one or more rows on the first internal surface; and an array of connection terminals on the second internal surface, where each connection terminal of the array of connection terminals is electrically connected to the electronics module.

In some embodiments, the header further comprises a moveable plate; the first internal surface of the cavity is a surface of the movable plate; and the header further comprises an actuator for driving the movable plate in a direction perpendicular to the central axis or plane of the cavity.

In some embodiments, the actuator comprises one or more set screws, a hydraulic bladder, a pneumatic bladder, a compression spring, a leaf spring, or a combination thereof.

In some embodiments, the array of connection terminals on the second internal surface are arranged in the same spatial configuration that spans one or more rows on the second internal surface.

In various embodiments, a medical device is provided comprising: an electronics module; and a header for connecting to the electronics module to a lead assembly. The header comprises: a housing comprising (i) a cavity having a central axis, a first internal surface, and a second internal surface located on a side of the cavity that is opposite of the first internal surface, and (ii) an opening aligned with the central axis or plane of the cavity; a first array of retractable contacts extending from the first internal surface towards the central axis or plane of the cavity, where retractable contacts of the first array of retractable contacts are arranged in a first spatial configuration that spans one or more rows on the first internal surface; a first array of connection terminals on the housing, where each connection terminal of the first array of connection terminals is: (i) electrically connected to the electronics module, and (i) electrically connectable to a retractable contact of the first array of retractable contacts; a second array of retractable contacts extending from the second internal surface towards the central axis or plane of the cavity, where retractable contacts of the second array of retractable contacts are arranged in a second spatial configuration that spans one or more rows on the second internal surface; and a second array of connection terminals on the housing, where each connection terminal of the second array of connection terminals is: (i) electrically connected to the electronics module, and (i) electrically connectable to a retractable contact of the second array of retractable contacts.

In some embodiments, the retractable contacts of the first array of retractable contacts and the second array of retractable contacts comprise: a body with a columnar shape, a tip with a semi-circular shape, and an actuator for driving the retractable contacts in a direction perpendicular to the central axis or plane of the cavity.

In some embodiments, the retractable contacts of the first array of retractable contacts and the second array of retractable contacts comprise: a body with a spherical shape that allows the retractable contacts to rotate in a first direction parallel to the central axis or plane of the cavity, and an actuator for driving the retractable contacts in a second direction perpendicular to the central axis or plane of the cavity.

In some embodiments, the actuator comprises: one or more set screws, a hydraulic bladder, a pneumatic bladder, a compression spring, a leaf spring, or a combination thereof.

In various embodiments, a medical device is provided comprising: an electronics module; and a header for connecting to the electronics module to a lead assembly. The header comprises: a housing comprising (i) a cavity having a central axis or plane and a fixed support, and (ii) an opening aligned with the central axis or plane of the cavity; an array of retractable contacts substantially embedded within the fixed support, where the retractable contacts are arranged in a spatial configuration that spans one or more rows within the fixed support; and an array of connection terminals on the housing, where each connection terminal of the array of connection terminals is: (i) electrically connected to the electronics module, and (i) electrically connectable to a retractable contact of the array of retractable contacts.

In some embodiments, the retractable contacts comprise: a body with a columnar shape, a tip with a semi-circular shape, and an actuator for driving the retractable contacts out of the fixed support in a direction perpendicular to the central axis or plane of the cavity.

In some embodiments, the retractable contacts comprise: a body with a spherical shape that allows the retractable contacts to rotate in a first direction parallel to the central axis or plane of the cavity, and an actuator for driving the retractable contacts out of the fixed support in a second direction perpendicular to the central axis or plane of the cavity.

In some embodiments, the actuator comprises: one or more set screws, a hydraulic bladder, a pneumatic bladder, a compression spring, a leaf spring, or a combination thereof.

In some embodiments, the header further comprises a removable locking mechanism that holds the retractable contacts embedded within the fixed support.

In some embodiments, the cavity further includes another fixed support located on a side of the cavity that is opposite of the fixed support.

In various embodiments, a medical device is provided comprising: an electronics module; and a header for connecting to the electronics module to a lead assembly. The header comprises: a moveable plate; a housing comprising (i) a cavity having a central axis, a first internal surface that is a surface of the moveable plate, and a second internal surface located on a side of the cavity that is opposite of the first internal surface, and (ii) an opening aligned with the central axis or plane of the cavity; an actuator for driving the movable plate in a direction perpendicular to the central axis or plane of the cavity; an array of retractable contacts extending from the first internal surface towards the central axis or plane of the cavity, where retractable contacts of the array of retractable contacts are arranged in a spatial configuration that spans one or more rows on the first internal surface; and an array of connection terminals on the housing or the moveable plate, where each connection terminal of the array of connection terminals is: (i) electrically connected to the electronics module, and (i) electrically connectable to a retractable contact of the array of retractable contacts.

In various embodiments, a medical device is provided comprising: an electronics module; and a header for connecting the electronics module to a lead assembly. The header comprises: a housing comprising (i) a cylindrical cavity having a central axis, a first internal surface that defines an inner diameter of the cylinder from the central axis, and a second internal surface that defines an outer diameter of the cylinder from the central axis and (ii) an opening aligned with the central axis of the cavity; an array of retractable contacts extending from the first internal surface towards the central axis of the cavity, where retractable contacts of the array of retractable contacts are arranged in a spatial configuration that spans one or more rows on the first internal surface; and an array of connection terminals on the second internal surface, where each connection terminal of the array of connection terminals is electrically connected to the electronics module.

In various embodiments, a medical device is provided comprises: an electronics module; and a header for connecting the electronics module to a lead assembly. The header comprising: a cylindrical projection having a central axis, an internal surface that is positioned on the central axis, and an external surface that defines an outer diameter of the cylindrical projection from the central axis; an array of retractable contacts extending from the external surface away from the central axis, where retractable contacts of the array of retractable contacts are arranged in a spatial configuration that spans one or more rows on the external surface; and an array of connection terminals on the internal surface, where each connection terminal of the array of connection terminals is electrically connected to the electronics module.

BRIEF DESCRIPTION OF THE DRAWINGS

The present invention will be better understood in view of the following non-limiting figures, in which.

DETAILED DESCRIPTION

I. Introduction

Figure 1:
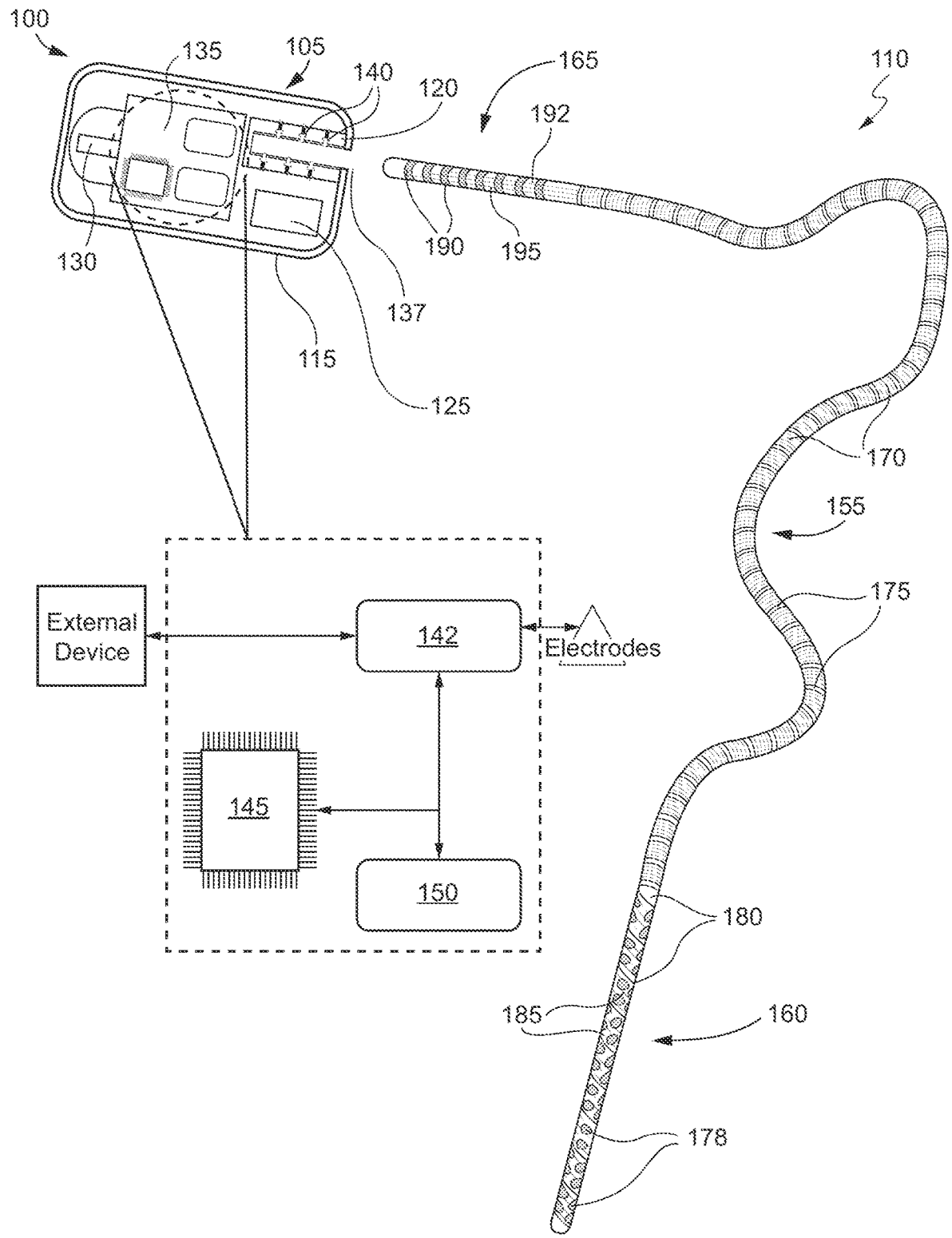
FIG. 1 shows a neuromodulation system in accordance with various embodiments.

The following disclosure describes connectors for high density neural interfaces and methods of microfabricating the connectors. In some embodiments, the connectors are located within or integral with the header of a device such as implantable neuromodulation device and used to connect the lead assembly with an electrical circuit of the neuromodulation device. Neuromodulation devices such as deep brain stimulators electrically interface with neural tissue and treat various neurological conditions through electrical stimulation. As described herein, conventional neuromodulation devices use between four and sixteen electrodes and comprise a neurostimulator and lead assembly containing the electrodes. The neuromodulation devices with high density neural interfaces (i.e., at least sixteen electrodes) for deep brain stimulation, cortical brain stimulation, spine stimulation, etc. often are limited in contact count by lead density, implant technique, connector density/pitch/size, or complexity (e.g., having a lead split to multiple connectors). However, higher density arrays are desired due to the ability to more closely focus energy during therapy in order to increase clinical effectiveness, reduce side effects due to errant charge, and increase battery life by using charge more efficiently.

Specifically, deep brain stimulation is a neurostimulation therapy that could greatly benefit from higher density arrays, which allows for higher resolution sensing and targeted current steering for stimulation. In many applications, the leads and neurostimulator (pulse generators) are separable components due to the additional flexibility of being able to explant one at a time rather than the entire system. Several technologies exist for making high density leads, for example thin film technology has been developed to increase the electrical traces available for connection to the neural interface. Similarly, microfabrication technology for high density circuit boards is well understood. The problem however lies in the interface between the lead and the electrical circuit on the pulse generator. The interconnections in the conventional header of a pulse generator are traditionally bulky and grow linearly with the number of connections. These interconnections are traditionally not scalable for high density technology.

To address these limitations and problems, the connectors of the present embodiments include structural features that have a three-dimensional design that is scalable for high density technology and capable of maintaining contact to contact pressure (i.e., maintain electrical connection between contacts of the header and contacts of the respective connector on the proximal end of the lead assembly). One illustrative embodiment of the present disclosure is directed to a medical device (e.g., an implantable medical device or a pulse generator) comprising: an electronics module; and a header for connecting the electronics module to a lead assembly, the header comprising: a housing comprising (i) a cavity having a central axis or plane and an internal surface, and (ii) an opening aligned with the central axis or plane of the cavity; an array of retractable contacts extending from the internal surface towards the central axis or plane of the cavity, where retractable contacts of the array of retractable contacts are arranged in a spatial configuration that spans one or more rows on the internal surface; and an array of connection terminals on the housing, where each connection terminal of the array of connection terminals is: (i) electrically connected to the electronics module, and (ii) electrically connectable to a retractable contact of the array of retractable contacts.

In other embodiments, a medical device (e.g., an implantable medical device or a pulse generator) is provided that comprises: an electronics module; and a header for connecting the electronics module to a lead assembly, the header comprising: a housing comprising (i) a cavity having a central axis, a first internal surface, and a second internal surface located on a side of the cavity that is opposite of the first internal surface, and (ii) an opening aligned with the central axis or plane of the cavity; an array of retractable contacts extending from the first internal surface towards the central axis or plane of the cavity, where retractable contacts of the array of retractable contacts are arranged in a spatial configuration that spans one or more rows on the first internal surface; and an array of connection terminals on the second internal surface, where each connection terminal of the array of connection terminals is electrically connected to the electronics module.

In other embodiments, a medical device (e.g., an implantable medical device or a pulse generator) is provided that comprises: an electronics module; and a header for connecting to the electronics module to a lead assembly, the header comprising: a housing comprising (i) a cavity having a central axis, a first internal surface, and a second internal surface located on a side of the cavity that is opposite of the first internal surface, and (ii) an opening aligned with the central axis or plane of the cavity; a first array of retractable contacts extending from the first internal surface towards the central axis or plane of the cavity, where retractable contacts of the first array of retractable contacts are arranged in a first spatial configuration that spans one or more rows on the first internal surface; a first array of connection terminals on the housing, where each connection terminal of the first array of connection terminals is electrically connected to: (i) the electronics module, and (ii) a retractable contact of the first array of retractable contacts; a second array of retractable contacts extending from the second internal surface towards the central axis or plane of the cavity, where retractable contacts of the second array of retractable contacts are arranged in a second spatial configuration that spans one or more rows on the second internal surface; and a second array of connection terminals on the housing, where each connection terminal of the second array of connection terminals is: (i) electrically connected to the electronics module, and (ii) electrically connectable to a retractable contact of the second array of retractable contacts.

In other embodiments, a medical device (e.g., an implantable medical device or a pulse generator) is provided that comprises: an electronics module; and a header for connecting to the electronics module to a lead assembly, the header comprising: a housing comprising (i) a cavity having a central axis or plane and a fixed support, and (ii) an opening aligned with the central axis or plane of the cavity; an array of retractable contacts substantially embedded within the fixed support, where the retractable contacts are arranged in a spatial configuration that spans one or more rows within the internal surface; and an array of connection terminals on the housing, where each connection terminal of the array of connection terminals is: (i) electrically connected to the electronics module, and (ii) electrically connectable to a retractable contact of the array of retractable contacts.

In other embodiments, a medical device (e.g., an implantable medical device or a pulse generator) is provided that comprises: an electronics module; and a header for connecting to the electronics module to a lead assembly, the header comprising: a moveable plate; a housing comprising (i) a cavity having a central axis, a first internal surface that is a surface of the moveable plate, and a second internal surface located on a side of the cavity that is opposite of the first internal surface, and (ii) an opening aligned with the central axis or plane of the cavity; an actuator for driving the movable plate in a direction perpendicular to the central axis or plane of the cavity; an array of retractable contacts extending from the first internal surface towards the central axis or plane of the cavity, where retractable contacts of the array of retractable contacts are arranged in a spatial configuration that spans one or more rows on the first internal surface; and an array of connection terminals on the housing or the moveable plate, where each connection terminal of the array of connection terminals is: (i) electrically connected to the electronics module, and (ii) electrically connectable to a retractable contact of the array of retractable contacts.

Advantageously, these approaches provide a connector for a header, which has increased contact points, a smaller footprint, and greater design flexibility. More specifically, these approaches enable connectors with reliable, non-permanent connections between a lead assembly and electrical circuit of the neuromodulation device. This solution is scalable to connecting many electrodes (e.g., greater than sixteen) (optionally using a multiplexer chip), and thus enabling several therapeutic opportunities for neurostimulation. Furthermore, even for applications where multiple electrodes are not required, various embodiments can be miniaturized to make the implant minimally invasive, additionally may make invasive anatomies to become accessible (or navigable) due to the miniaturization. It should be understood that although deep brain neurostimulation device applications are provided as examples of some embodiments, this solution is applicable to all leads and devices that need electrodes/sensors attached to a neurostimulator.

II. Neuromodulation Devices and Systems with a Lead Assembly

FIG. 1 shows a neuromodulation system 100 in accordance with some aspects of the present invention. In various embodiments, the neuromodulation system 100 includes an implantable neurostimulator 105 and a lead assembly 110. The implantable neurostimulator 105 (e.g., an implantable pulse generator (IPG)) may include a housing 115, a connector stack or header 120, a power source 125, an antenna 130, and an electronics module 135 (e.g., a computing system). The housing 115 may be comprised of materials that are biocompatible such as bioceramics or bioglasses for radio frequency transparency, or metals such as titanium. In accordance with some aspects of the present invention, the size and shape of the housing 115 may be selected such that the neurostimulator 105 can be implanted within a patient. In the example shown in FIG. 1, the connector stack or header 120 is attached to an opening 137 in a surface of the housing 115 in a manner such that the housing 115 is hermetically sealed. The connector stack or header 120 may include one or more contacts 140 (i.e., electrically conductive elements, pins, wires, tabs, pads, etc.) mounted within the housing 115 or a cap extending from an interior to an exterior of the housing 115. The one or more contacts 140 are arranged (e.g., as a female connector) to match and make electrical contact with one or more contacts of a connector (e.g., a male connector) of the lead assembly 110. In various embodiments, the contacts 140 may be made with a hemisphere on contact (point contact) or with a cylinder on contact (line contact). In some embodiments, the contacts 140 are spring-loaded normal to the outer contact surfaces of the contacts of the connector. The power source 125 may be within the housing 115 and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry. A used herein, "electrically connected" or "electrically interfaced" means an electrical circuit (path or line through which an electrical current flows) is created between the two or more components that are connected or interfaced. The connection or interface between the two or more components may be permanent or temporary.

In some embodiments, the electronics module 135 may be connected (e.g., electrically connected) to interior ends of the connector stack or header 120 such that the electronics module 135 is able to apply a signal or electrical current to conductive traces of the lead assembly 110 connected to the connector stack or header 120. The electronics module 135 may include discrete and/or integrated electronic circuit components that implement analog and/or digital circuits capable of producing the functions attributed to the neuromodulation devices or systems such as applying or delivering neural stimulation to a patient. In various embodiments, the electronics module 135 may include software and/or electronic circuit components such as a pulse generator 142 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), and/or causes delivery of the stimulation via the pulse generator 140 and electrodes, and a memory 150 with program instructions operable on by the pulse generator 140 and the controller 145 to perform one or more processes for applying or delivering neural stimulation.

In various embodiments, the lead assembly 110 includes one or more cables or lead bodies 155, one or more electrode assemblies 160, and one or more connectors 165, as discussed in further detail herein. The one or more cables 155 may include one or more conductive traces 170 formed on a supporting structure 175. The one or more electrode assemblies 160 may include one or more electrodes 178 and/or sensors formed on a supporting structure 180 using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). The one or more electrodes 178 may be in electrical connection with one or more conductive traces 185. The one or more connectors 165 may include one or more conductive contacts 190 formed on a supporting structure 192 in electrical connection with one or more conductive traces 195.

In some embodiments, the lead assembly 110 is a monolithic structure, polylithic structure, or a combinations of monolithic and polylithic structures. For example, the one or more cables or lead bodies 155, the one or more electrode assemblies 160, and the one or more connectors 165 may all be fabricated using a same layer of base material (monolithic). In other words, the supporting structures 175, 180, 192 may be a continuous layer of base material (e.g., one or more layers of dielectric material). Moreover, the one or more conductive traces 170, 185, 195 may all be fabricated using a same layer of conductive material. In other words, the one or more conductive traces 170, 185, 195 may be a continuous layer of conductive material (e.g., one or more layers of conductive material). Alternatively, the one or more cables or lead bodies 155, the one or more electrode assemblies 160, and the one or more connectors 165 may be fabricated using different layers or combinations of the same and different layers of base material that are connected together (polylithic or a combination of monolithic and polylithic). In other words, the supporting structures 175, 180, 192 may include various layers of base material (e.g., one or more layers of dielectric material) that interconnected together or a combination of continuous and interconnected layers of base material. Moreover, the one or more conductive traces 170, 185, 195 may all be fabricated using different layers or combinations of the same and different layers of conductive material. In other words, the one or more conductive traces 170, 185, 195 may be interconnected layers or a combination of continuous and interconnected layers of conductive material (e.g., one or more layers of conductive material).

III. Pulse Generators and Header Connectors

Figure 2:
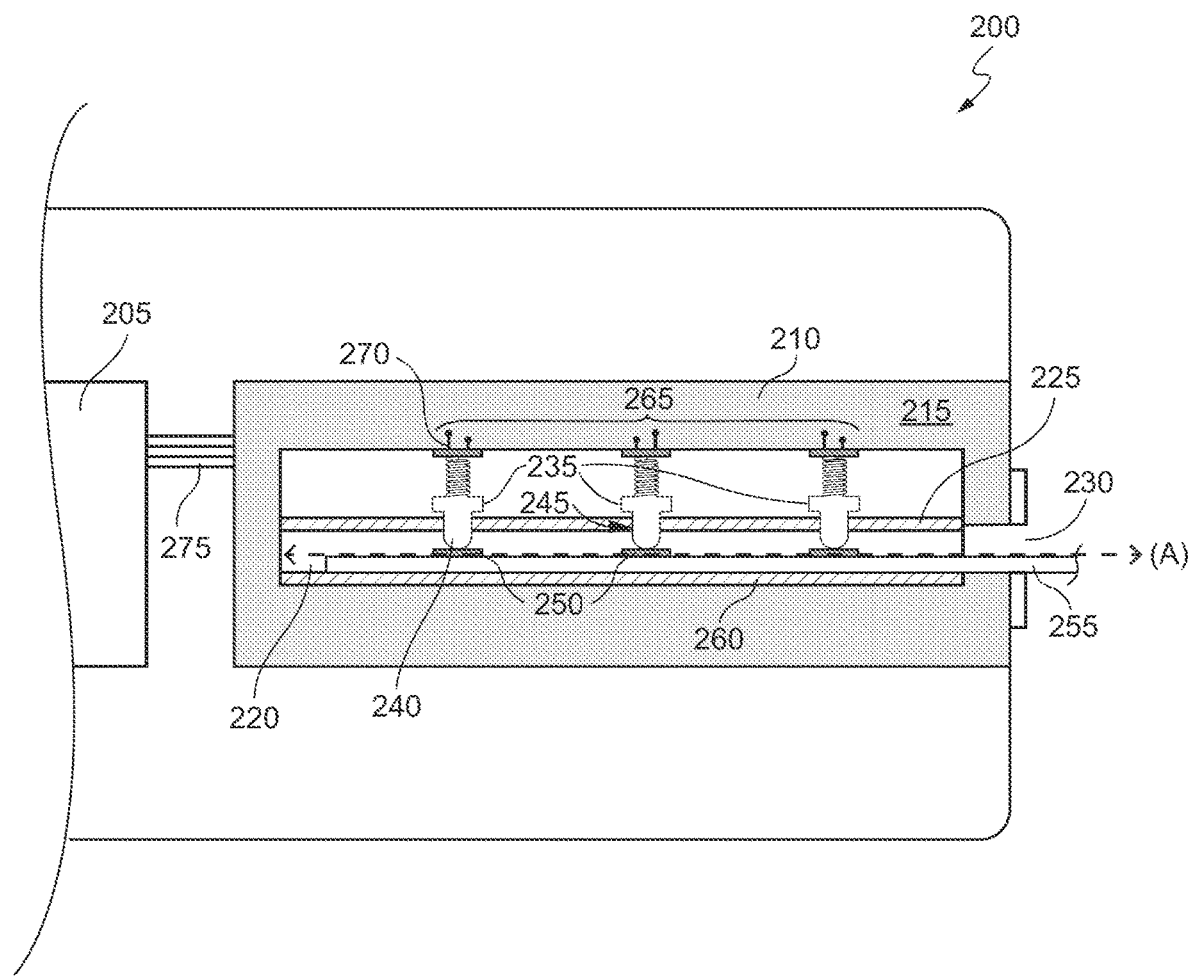
FIG. 2 shows a header for a pulse generator in accordance with various embodiments.

FIG. 2 shows a pulse generator 200 (e.g., the implantable neurostimulator 105 described with respect to FIG. 1) in accordance with aspects of the present disclosure. In various embodiments, the pulse generator 200 comprises an electronics module 205 and a connector stack or header 210 for connecting to the electronics module 205 to a lead assembly (shown in FIG. 1). In some embodiments, the header 210 comprises a housing 215 comprising (i) a cavity 220 having a central axis or plane (A) and an internal surface 225, and (ii) an opening 230 aligned with the central axis or plane (A) of the cavity 220. As used herein, "aligned" means that the components are arranged in a straight line (e.g., along axis or plane (A)).

The header 210 further comprises an array of retractable contacts 235 extending from the internal surface 225 towards the central axis or plane (A) of the cavity 220. The retractable contacts 240 of the array of retractable contacts 235 may be arranged in a spatial configuration that spans one or more rows on the internal surface 225. The retractable contacts 240 can be located in a spatial configuration such that each of the retractable contacts 240 can be aligned to correspond with contacts 250 of a respective connector 255. For example, the spatial configuration may be staggered, aligned, wavy, honeycomb, arbitrary speckled, diagonal, grid, checkerboard, circular, annular, haring bone, periodic, or a combination thereof. The spatial configuration allows the header 210 to accommodate connectors with varying numbers of electrical contacts. In some embodiments, retractable contacts 240 are integrated into the header geometry in such a way that there is a "mechanical interference" of the retractable contacts 240 in its actuated state and the connector (e.g., interference cause by mechanical pressure from an opposing set of retractable contacts or an opposing internal surface/fixed support 260). This "mechanical interference" creates the normal force to maintain the electrical connection between the retractable contacts 240 and the contacts 250 of the connector 255.

The header 210 further comprises an array of connection terminals 265 on the housing 215. One or more of the connection terminals 270 of the array of connection terminals 265 is: (i) electrically connected to the electronics module 205 (see, e.g., wiring layer or feedthrough 275), and (ii) electrically connectable to a retractable contact 240 of the array of retractable contacts 245 (conductive with one another when retractable contact is in predetermined position). In various embodiments, the connection terminals 270 are comprised of one or more layers of conductive material. The conductive material selected for the connection terminals 270 should be biocompatible, have good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, at least one connection terminal 270 from the array of connection terminals 265 terminates at a retractable contact 240. Alternatively, each connection terminal 270 from the array of connection terminals 265 terminates at a retractable contact 240. Alternatively, the connection terminals 270 may terminate to a single retractable contact 240 or a single connection terminal terminates at multiple retractable contacts 240, or multiple connection terminals 270 are wired in parallel (these connections may be made further upstream within the structure of 215 or routed through 275).

As should be understood, in some embodiments, each retractable contact 240 from the header 210 is electrically connectable to a respective connection terminal 270. In other words, each retractable contact 240 may be electrically connected to a different connection terminal 270 (a one to one relationship). In alternative embodiments, the retractable contacts 240 or the connection terminals 270 may be structured such that sets of retractable contacts 240 (multiple retractable contacts 240) or sets of connection terminals 270 (multiple connection terminals 270) are electrically connectable to a respective connection terminal 270 or retractable contact 240. In other words, each connection terminal 270 or retractable contact 240 may be electrically connected to a same or different connection terminal 270 or retractable contact 240 (a many to one relationship).

Figure 3A:
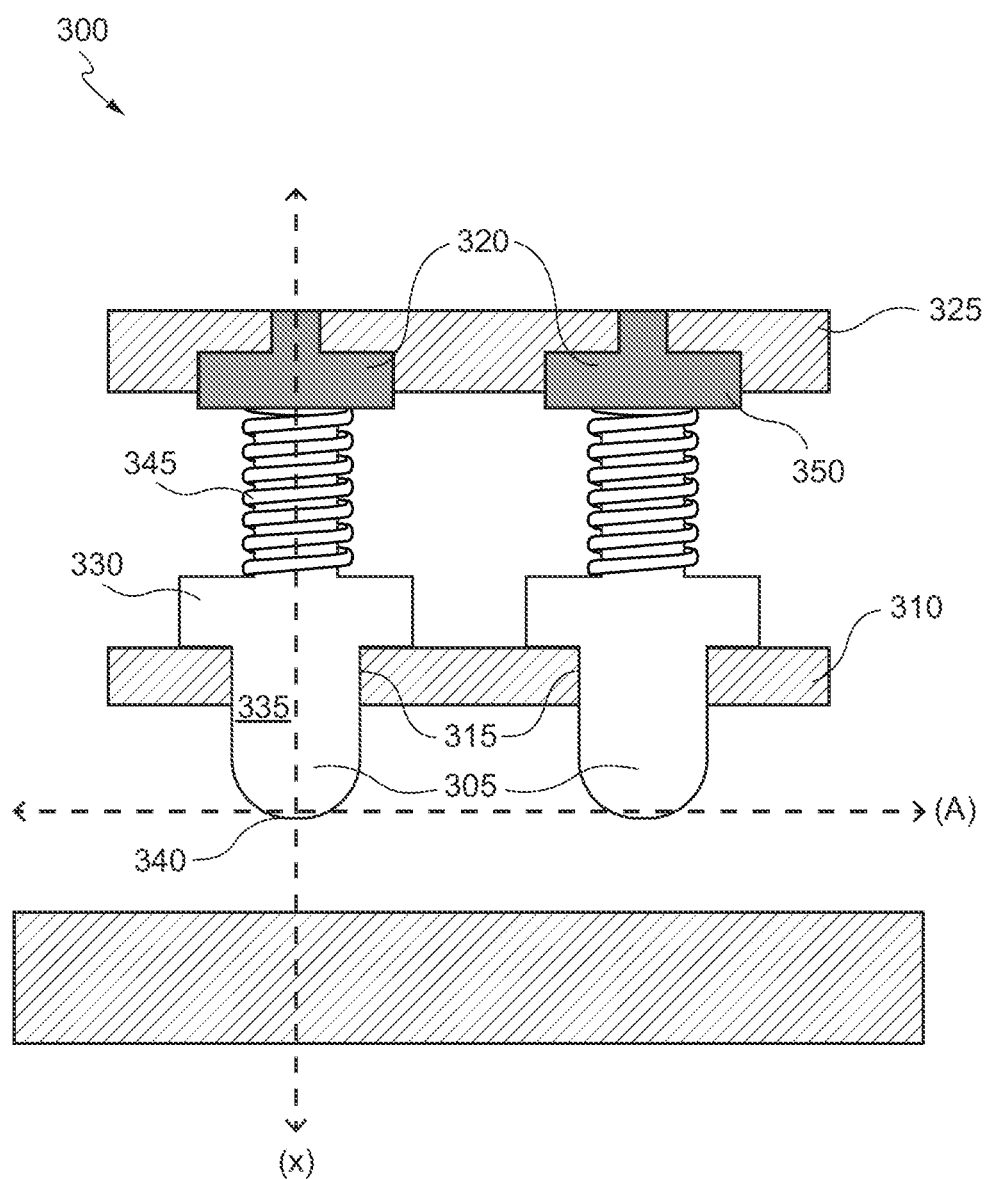
FIGS. 3A and 3B show a detailed view of retractable connectors in accordance with various embodiments.
Figure 3B:
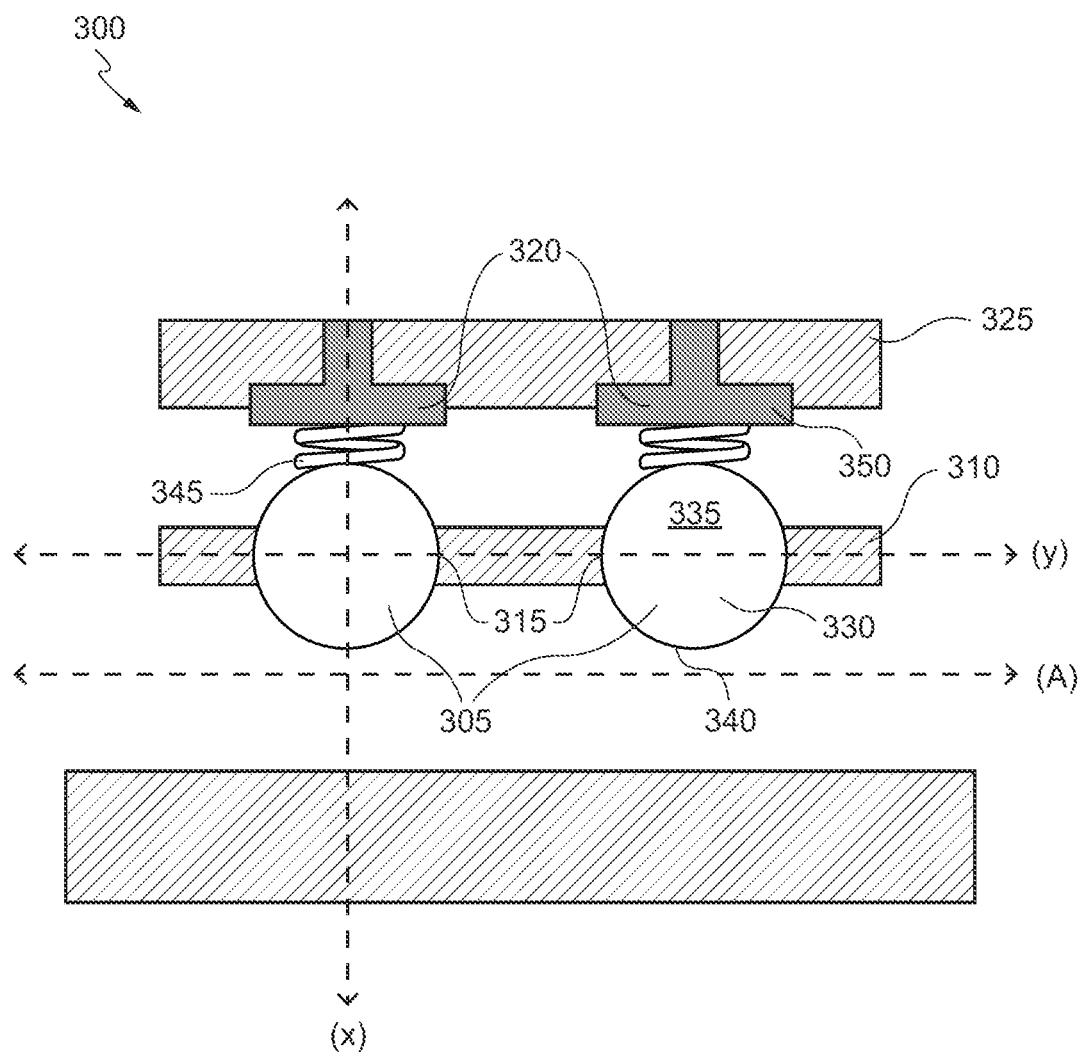

FIG. 3A shows a detailed view of a header 300 comprising an array of retractable contacts 305 (e.g., the array of retractable contacts 235 described with respect to FIG. 2). The internal surface 310 (an insulated body) has a plurality of contact slots 315 vertically defined through the internal surface 310, and a plurality of connection terminal slots 320 within the housing 325 and respectively aligned with the contact slots 315. The retractable contacts 330 of the array of retractable contacts 305 comprise a body 335 with a shape such as a columnar shape, a tip 340 with a shape such as a semi-circular shape, and an actuator 345 for driving the retractable contacts 305 on an axis (X) perpendicular to the central axis or plane (A) of the cavity. The body 335 of each of the retractable contacts 330 may be partially disposed within the contact slots 315. The actuator 345 may comprise one or more set screws, a hydraulic bladder, a pneumatic bladder, a compression spring (as shown in FIGS. 3A and 3B), a leaf spring, or a combination thereof. Connection terminals 350 are respectively disposed within the connection terminal slots 320.

FIG. 3B shows a detailed view of the header 300 comprising an alternative array of retractable contacts 305 (e.g., the array of retractable contacts 235 described with respect to FIG. 2). The internal surface 310 (an insulated body) has a plurality of contact slots 315 vertically defined through the internal surface 310, and a plurality of connection terminal slots 320 within the housing 325 and respectively aligned with the contact slots 315. The retractable contacts 330 of the array of retractable contacts 305 comprise a body 335 with a shape such as a spherical shape, a contact surface 340 with a shape such as a circular shape, and an actuator 345 for driving the retractable contacts 305 on an axis (X) perpendicular to the central axis or plane (A) of the cavity. The body 335 of each of the retractable contacts 330 may be partially disposed within the contact slots 315. In this embodiment, because of the spherical nature of the body 335, the retractable contacts 330 can be actuated forward in one main axis (X) (perpendicular to the central axis or plane (A) of the cavity or perpendicular to connector insertion) and can also move freely in an axis (Y) parallel to the central axis or plane (A) of the cavity or lead insertion) (e.g., metal balls actuated forward by spring but can also roll along lead insertion direction). The actuator 345 may comprise one or more set screws, a hydraulic bladder, a pneumatic bladder, a compression spring (as shown in FIGS. 3A and 3B), a leaf spring, or a combination thereof. Connection terminals 350 are respectively disposed within the connection terminal slots 320.

The operation principle of the header 300 according to the various embodiments is as follows. When the connection terminals 350 respectively abut against an insulated member or air gap (e.g., a sleeve or collar, which could be a portion of the actuator 345) before the retractable contacts 330 are actuated to a predetermined position, the connection terminals 350 and the retractable contacts 330 are not conductive with each other. When the retractable contacts 330 are actuated to the predetermined position, the retractable contacts 330 and the connection terminals 350 are conductive with each other. In some embodiments, the actuator 345 is actuated by contact pressure or compressive pressure supplied by insertion of the connector in the cavity of the header 300. In some embodiments, the actuator 345 is turned on/off upon full connector insertion (e.g., deflating an air bladder to allow easy retraction of the contacts when the connector is being inserted and then when the connector is fully inserted into place, inflate the bladder to push the retractable contacts 330 forward). In some embodiments, the header 300 further comprises a removable locking mechanism that holds the retractable contacts 340 embedded within the fixed support 310.

Figure 4:
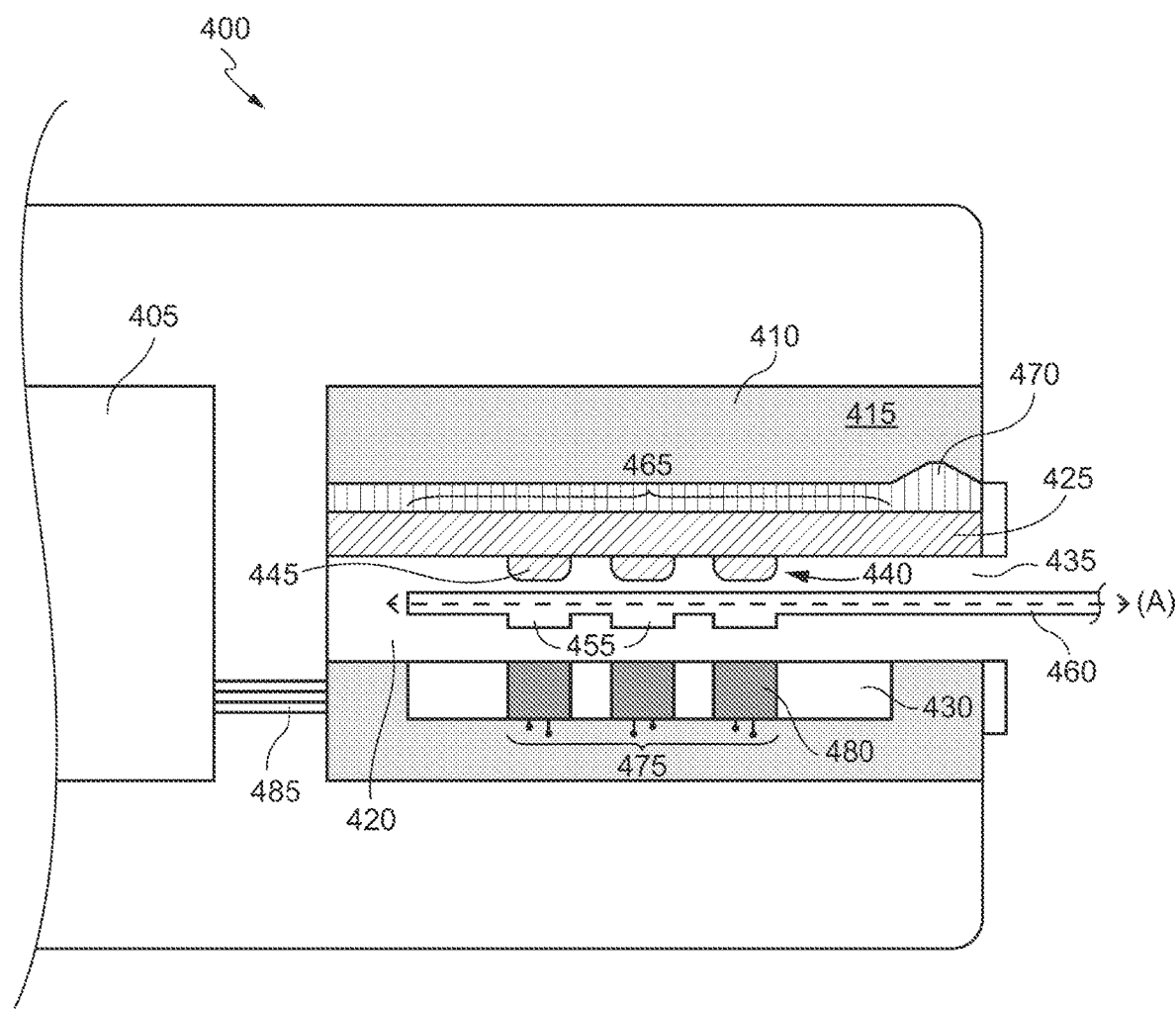
FIG. 4 shows a header with a moveable plate in accordance with various embodiments.

FIG. 4 shows an alternative pulse generator 400 (e.g., the implantable neurostimulator 105 described with respect to FIG. 1) in accordance with aspects of the present disclosure. In various embodiments, the pulse generator 400 comprises an electronics module 405 and a header 410 for connecting to the electronics module 405 to a lead assembly (shown in FIG. 1). In some embodiments, the header 410 comprises a housing 415 comprising (i) a cavity 420 having a central axis or plane (A), a first internal surface 425, and a second internal surface 430 located on a side of the cavity 420 that is opposite of the first internal surface 425, and (ii) an opening 435 aligned with the central axis or plane (A) of the cavity 420.

The header 410 further comprises an array of retractable contacts 440 extending from the first internal surface 425 towards the central axis or plane (A) of the cavity 420. The retractable contacts 445 of the array of retractable contacts 440 may be arranged in a spatial configuration that spans one or more rows on the first internal surface 425. In some embodiments, the array of retractable contacts 440, as shown, are not electrical contacts but instead serve to more directly apply the normal contact force on the area of contacts 455 and not waste that force on the inter-conductor space of the connector 460. In some embodiments, the first internal surface 425 that provides the normal force is on the non-conducting side (as shown in FIG. 4) or on the conducting side. In some embodiments, the contacts 455 and array of conducting terminals 475 may be on the fixed side (as shown in FIG. 4) or on the actuating side of the moveable plate 465.

The retractable contacts 445 can be located in a spatial configuration such that each of the retractable contacts 445 can be aligned to correspond with contacts 455 of the connector 460. For example, the spatial configuration may be staggered, aligned, wavy, honeycomb, arbitrary speckled, diagonal, grid, checkerboard, circular, annular, haring bone, periodic, or a combination thereof. The spatial configuration allows the header 410 to accommodate connectors with varying numbers of electrical contacts. In some embodiments, retractable contacts 445 are integrated into the header geometry in such a way that there is a "mechanical interference" of the retractable contacts 445 in its actuated state and the connector (e.g., interference cause by mechanical pressure from an opposing set of retractable contacts or the opposing second internal surface 430). This "mechanical interference" creates the normal force to maintain the electrical connection between the retractable contacts 445 and the contacts 455 of the connector 460.

In some embodiments, the header 410 further comprises a moveable plate 465 where the first internal surface 425 of the cavity 420 is a surface of the movable plate 465. In some embodiments, the header 410 further comprise an actuator 470 for driving the moveable plate 465 in a direction perpendicular to the central axis or plane (A) of the cavity 420. The actuator 470 may comprise one or more set screws, a hydraulic bladder (shown in FIG. 4), a pneumatic bladder, a compression spring, a leaf spring, or a combination thereof.

The header 410 further comprises an array of connection terminals 475 on the second internal surface 430. One or more of the connection terminals 480 of the array of connection terminals 475 is electrically connected to the electronics module 405 (see, e.g., wiring layer or feedthrough 485). In various embodiments, the connection terminals 480 are comprised of one or more layers of conductive material. The conductive material selected for the connection terminals 480 should be biocompatible, have good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, the array of connection terminals 475 on the second internal surface 430 are arranged in the same spatial configuration that spans one or more rows on the second internal surface 430. The connection terminals 480 can be located in a spatial configuration such that each of the connection terminals 480 can be aligned to correspond with the contacts 455 of the connector 460.

Figure 5A:
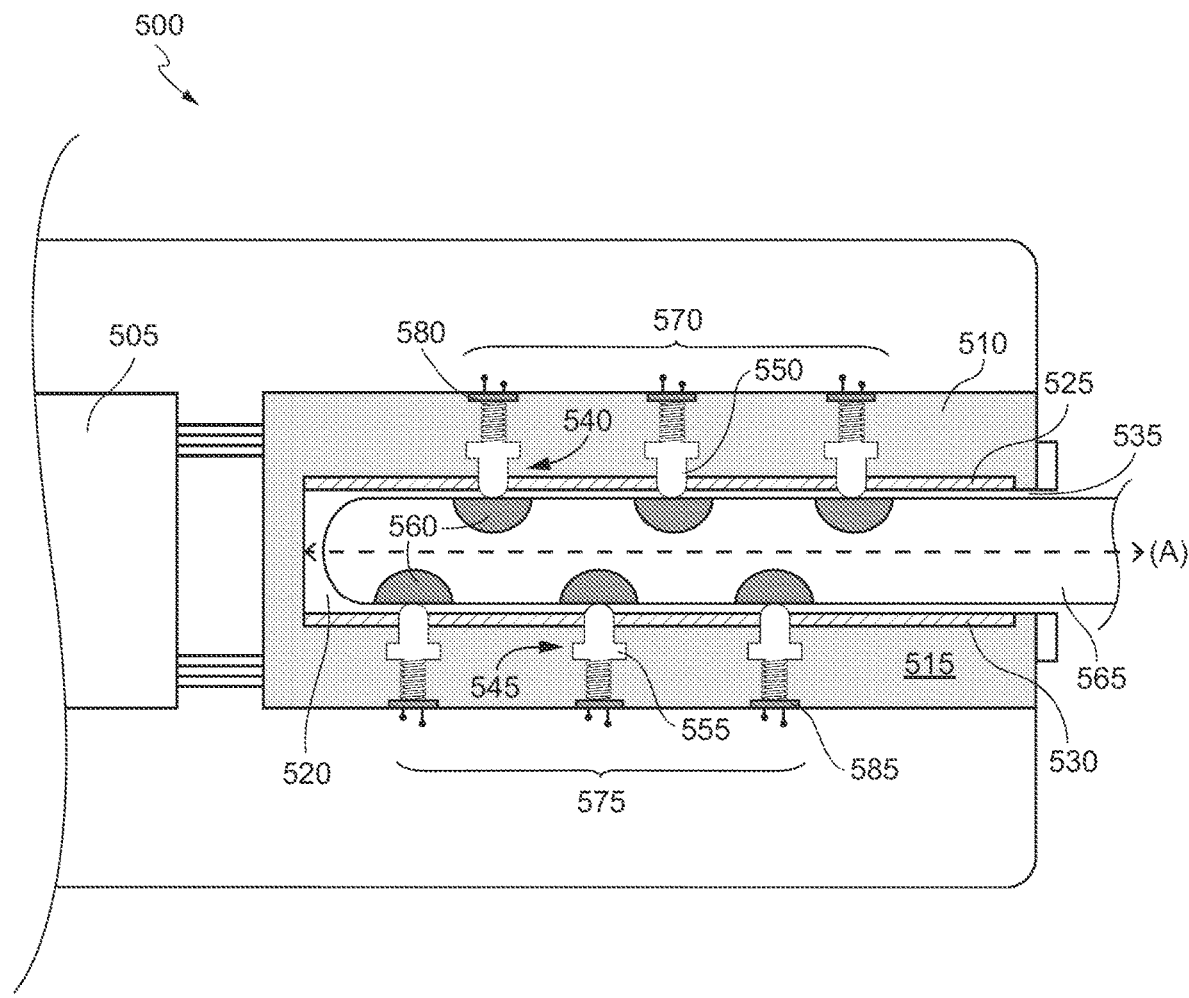
FIGS. 5A-5C show alternative headers for a pulse generator in accordance with various embodiments.

FIG. 5A shows an alternative pulse generator 500 (e.g., the implantable neurostimulator 105 described with respect to FIG. 1) in accordance with aspects of the present disclosure. In various embodiments, the pulse generator 500 comprises an electronics module 505 and a header 510 for connecting to the electronics module 505 to a lead assembly (shown in FIG. 1). In some embodiments, the header 510 comprises a housing 515 comprising (i) a cavity 520 having a central axis or plane (A), a first internal surface 525, and a second internal surface 530 located on a side of the cavity 520 that is opposite of the first internal surface 525, and (ii) an opening 535 aligned with the central axis or plane (A) of the cavity 520.

The header 510 further comprises a first array of retractable contacts 540 extending from the first internal surface 525 towards the central axis or plane (A) of the cavity 520, and a second array of retractable contacts 545 extending from the second internal surface 530 towards the central axis or plane (A) of the cavity 520 (e.g., the array of retractable contacts 305 described with respect to FIGS. 3A and 3B). The retractable contacts 550 of the first array of retractable contacts 540 may be arranged in a first spatial configuration that spans one or more rows on the first internal surface 525. The retractable contacts 555 of the second array of retractable contacts 545 may be arranged in a second spatial configuration that spans one or more rows on the second internal surface 530. The first spatial configuration and the second spatial configuration may be the same or different spatial configuration. The retractable contacts 550, 555 can be located in a spatial configuration such that each of the retractable contacts 550, 555 can be aligned to correspond with contacts 560 of a respective connector 565. For example, the first spatial configuration and the second spatial configuration may be staggered, aligned, wavy, honeycomb, arbitrary speckled, diagonal, grid, checkerboard, circular, annular, haring bone, periodic, or a combination thereof. The first spatial configuration and the second spatial configuration allows the header 510 to accommodate connectors with varying numbers of electrical contacts. In some embodiments, retractable contacts 550, 555 are integrated into the header geometry in such a way that there is a "mechanical interference" of the retractable contacts 550, 555 in its actuated state and the connector (e.g., interference cause by mechanical pressure from an opposing set of retractable contacts 550, 555 or the opposing internal surfaces 525, 530). This "mechanical interference" creates the normal force to maintain the electrical connection between the retractable contacts 550, 555 and the contacts 560 of the connector 565.

The header 510 further comprises a first array of connection terminals 570 on the housing 515 and a second array of connection terminals 575 on the housing 515. One or more of the connection terminals 580 of the first array of connection terminals 570 is electrically connected to the electronics module 505 and electrically connectable to the first array of retractable contacts 540. In certain embodiments, each of the connection terminals 580 of the first array of connection terminals 570 is electrically connected to the electronics module 505 and electrically connectable to the first array of retractable contacts 540. One or more of the connection terminals 585 of the second array of connection terminals 575 is electrically connected to the electronics module 505 and electrically connectable to the second array of retractable contacts 545. In certain embodiments, each of the connection terminals 585 of the second array of connection terminals 575 is electrically connected to the electronics module 505 and electrically connectable to the second array of retractable contacts 545. In various embodiments, the connection terminals 580, 585 are comprised of one or more layers of conductive material. The conductive material selected for the connection terminals 580, 585 should be biocompatible, have good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof.

Figure 5B:
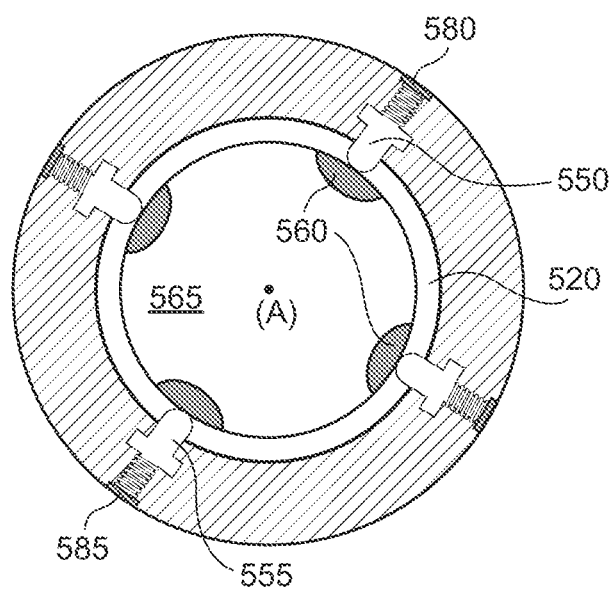

Certain applications have leads where the proximal end's array of contacts 560 are positioned around a common axis to form a cylindrical structure (as shown in FIG. 5A). For example, the spatial configuration of the array of contacts around the common axis may be staggered, aligned, wavy, honeycomb, arbitrary speckled, diagonal, grid, checkerboard, circular, annular, haring bone, periodic, or a combination thereof. Configurations similar to the ones described herein can easily be reconfigured to accept a cylindrical proximal end. In this form, it is possible to have the contacts 560 facing outward from the connector 565 at proximal end of the lead (as a solid structure) (as shown in FIGS. 5A and 5B). In such an instance, the header 510 may comprise a housing comprising (i) a cylindrical cavity having a central axis, a first internal surface that defines an inner diameter of the cylinder from the central axis, and a second internal surface that defines an outer diameter of the cylinder from the central axis and (ii) an opening aligned with the central axis of the cavity. The header may further comprise an array of retractable contacts extending from the first internal surface towards the central axis of the cavity, where retractable contacts of the array of retractable contacts are arranged in a spatial configuration that spans one or more rows on the first internal surface. The header may further comprise an array of connection terminals on the second internal surface, where each connection terminal of the array of connection terminals is electrically connected to the electronics module.

Figure 5C:
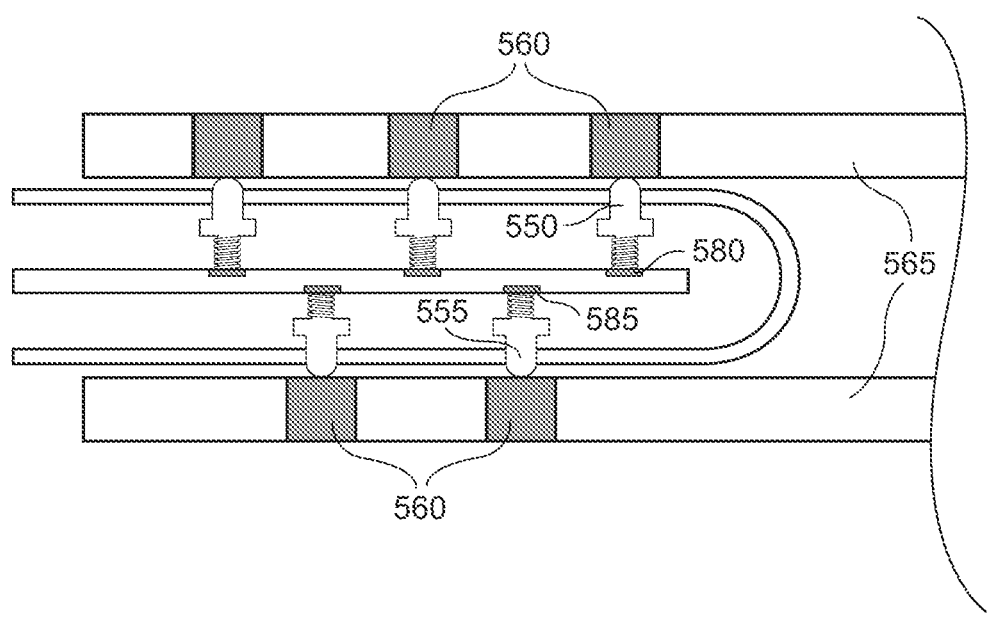

Alternatively, it is possible to have the contacts 560 facing inward from the connector 565 at proximal end of the lead (as a hollow structure) (as shown in FIG. 5C) to protect the contacts 560 from handling damage. In such an instance, the header may comprise a cylindrical projection having a central axis, an internal surface that is positioned on the central axis, and an external surface that defines an outer diameter of the cylindrical projection from the central axis. The header may further comprise an array of retractable contacts extending from the external surface away from the central axis, where retractable contacts of the array of retractable contacts are arranged in a spatial configuration that spans one or more rows on the external surface. The header may further comprise an array of connection terminals on the internal surface, where each connection terminal of the array of connection terminals is electrically connected to the electronics module.

Figure 6:
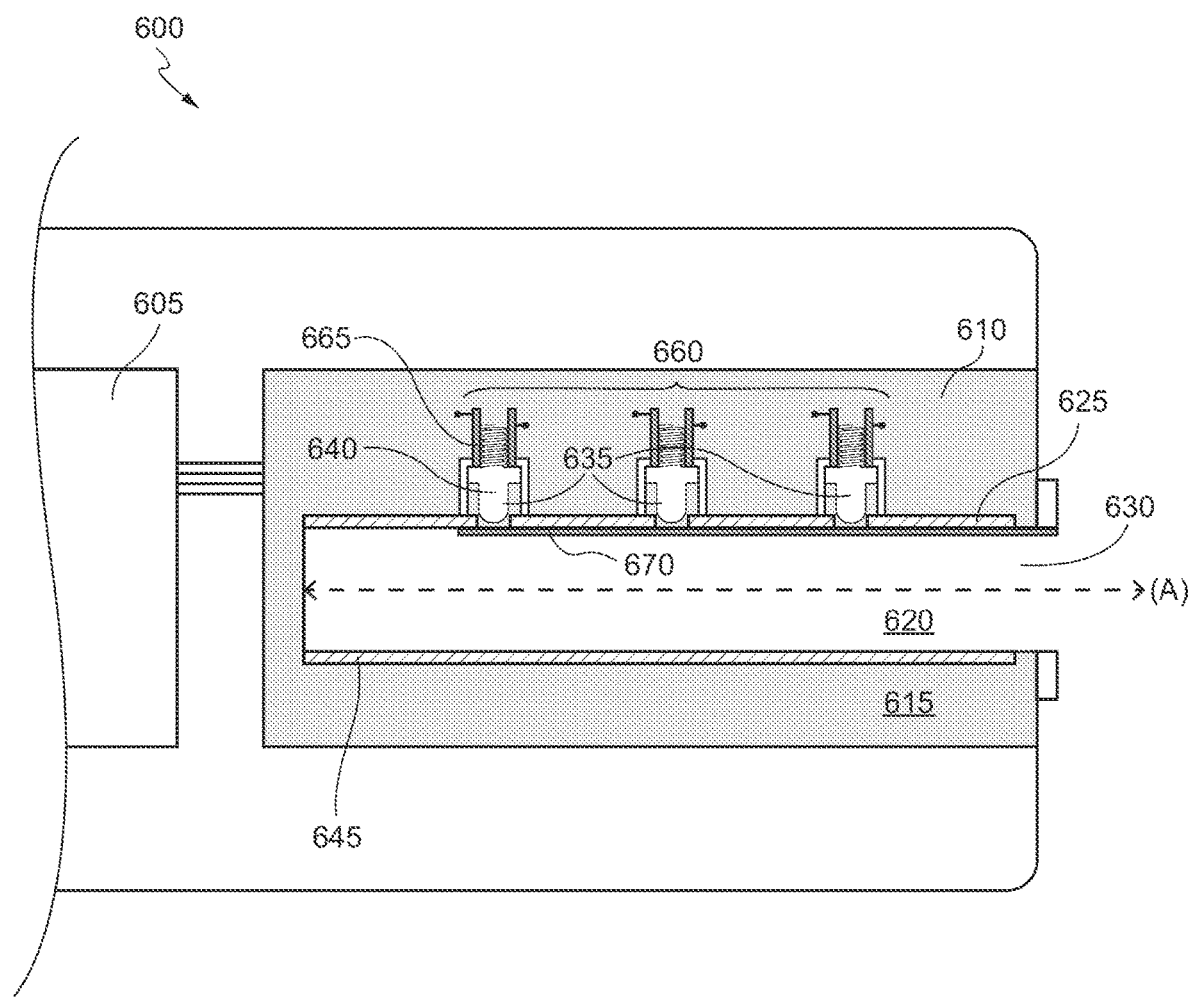
FIG. 6 shows an alternative header for a pulse generator in accordance with various embodiments.

FIG. 6 shows a pulse generator 600 (e.g., the implantable neurostimulator 105 described with respect to FIG. 1) in accordance with aspects of the present disclosure. In various embodiments, the pulse generator 600 comprises an electronics module 605 and a header 610 for connecting to the electronics module 605 to a lead assembly (shown in FIG. 1). In some embodiments, the header 610 comprises a housing 615 comprising (i) a cavity 620 having a central axis (A) and a fixed support 625, and (ii) an opening 630 aligned with the central axis (A) of the cavity 620.

The header 610 further comprises an array of retractable contacts 635 substantially embedded within the fixed support 625 (e.g., the array of retractable contacts 305 described with respect to FIGS. 3A and 3B). As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. The retractable contacts 640 of the array of retractable contacts 635 may be arranged in a spatial configuration that spans one or more rows within the fixed support 625. The retractable contacts 640 can be located in a spatial configuration such that each of the retractable contacts 640 can be aligned to correspond with contacts of a respective connector. For example, the spatial configuration may be staggered, aligned, wavy, honeycomb, arbitrary speckled, diagonal, grid, checkerboard, circular, annular, haring bone, periodic, or a combination thereof. The spatial configuration allows the header 610 to accommodate connectors with varying numbers of electrical contacts. In some embodiments, retractable contacts 640 are integrated into the header geometry in such a way that there is a "mechanical interference" of the retractable contacts 640 in its actuated state and the connector (e.g., interference cause by mechanical pressure from an opposing set of retractable contacts or an opposing internal surface/fixed support 645). This "mechanical interference" creates the normal force to maintain the electrical connection between the retractable contacts 640 and the contacts of the connector.

The header 610 further comprises an array of connection terminals 660 on the housing 615. One or more of the connection terminals 665 of the array of connection terminals 660 is electrically connected to the electronics module 605, and electrically connectable to a retractable contact 640 of the array of retractable contacts 645. In some embodiments, each of the connection terminals 665 of the array of connection terminals 660 is electrically connected to the electronics module 605, and electrically connectable to a retractable contact 640 of the array of retractable contacts 645. In various embodiments, the connection terminals 665 are comprised of one or more layers of conductive material. The conductive material selected for the connection terminals 665 should be biocompatible, have good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, at least one connection terminal 665 from the array of connection terminals 660 terminates at a retractable contact 640. Alternatively, each connection terminal 665 from the array of connection terminals 660 terminates at a retractable contact 640.

As should be understood, in some embodiments, each retractable contact 640 from the header 610 is electrically connectable to a respective connection terminal 665. In other words, each retractable contact 640 may be electrically connected to a different connection terminal 665 (a one to one relationship). In alternative embodiments, the retractable contacts 640 or the connection terminals 665 may be structured such that sets of retractable contacts 640 (multiple retractable contacts 640) or sets of connection terminals 665 (multiple connection terminals 665) are electrically connectable to a respective connection terminal 665 or retractable contact 640. In other words, each connection terminal 665 or retractable contact 640 may be electrically connected to a same or different connection terminal 665 or retractable contact 640 (a many to one relationship).

In some embodiments, the header 610 further comprises a removable locking mechanism 670 (e.g., a removable sleeve or film) that holds the retractable contacts 640 embedded within the fixed support 625. In some embodiments, the cavity 620 further comprises another fixed support 645 located on a side of the cavity 620 that is opposite of the fixed support 625.

Figure 7:
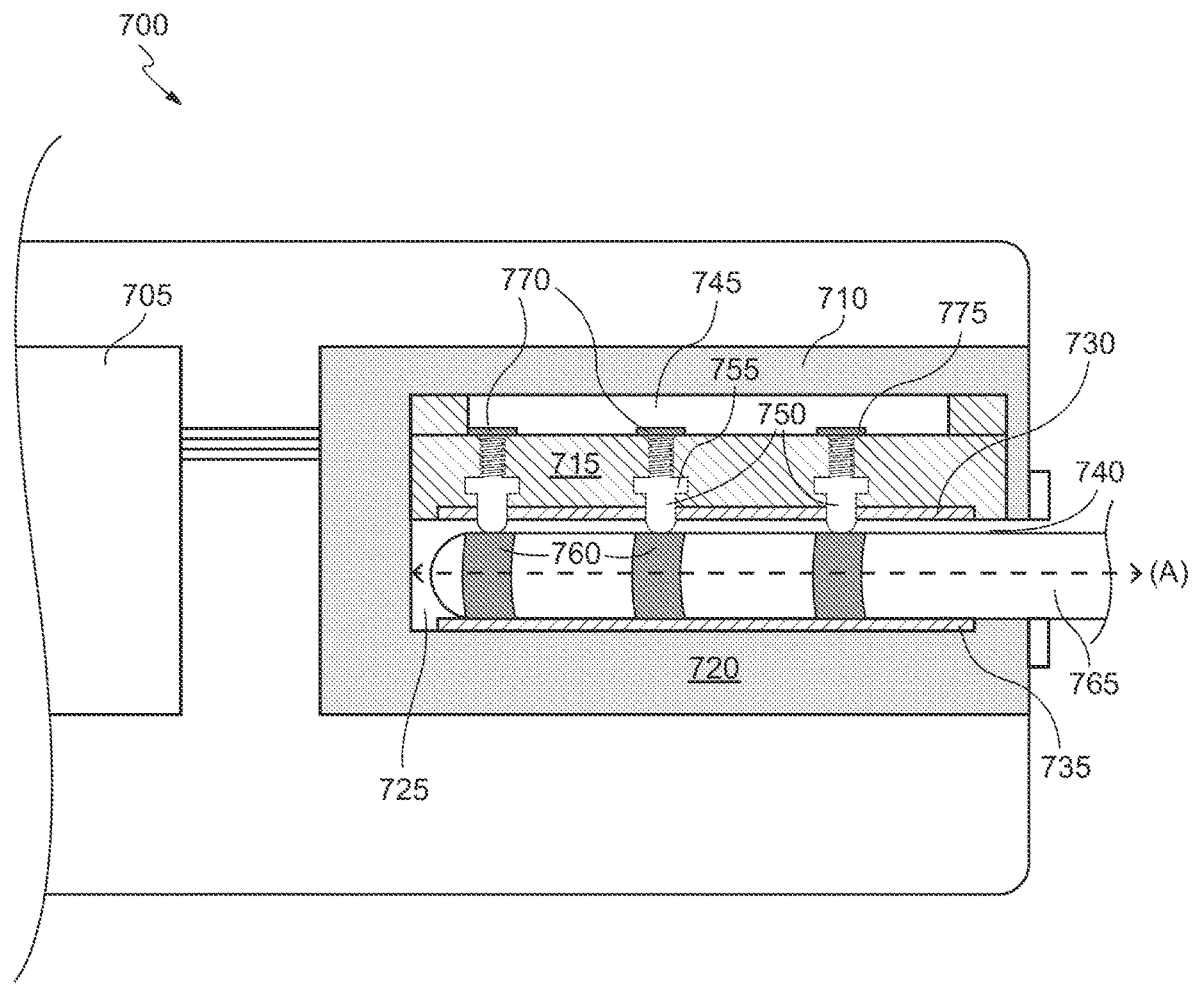
FIG. 7 shows an alternative header with a moveable plate in accordance with various embodiments.

FIG. 7 shows an alternative pulse generator 700 (e.g., the implantable neurostimulator 105 described with respect to FIG. 1) in accordance with aspects of the present disclosure. In various embodiments, the pulse generator 700 comprises an electronics module 705 and a header 710 for connecting to the electronics module 705 to a lead assembly (shown in FIG. 1). In some embodiments, the header 710 comprises a moveable plate 715 and a housing 720 comprising (i) a cavity 725 having a central axis or plane (A), a first internal surface 730 that is a surface of the moveable plate 715, and a second internal surface 735 located on a side of the cavity 725 that is opposite of the first internal surface 730, and (ii) an opening 740 aligned with the central axis or plane (A) of the cavity 725.

The header 710 further comprises an actuator 745 for driving the movable plate 715 in a direction perpendicular to the central axis or plane (A) of the cavity 725. The actuator 745 may comprise one or more set screws, a hydraulic bladder (shown in FIG. 7), a pneumatic bladder, a compression spring, a leaf spring, or a combination thereof.

The header further comprises an array of retractable contacts 750 extending from the first internal surface 730 towards the central axis or plane (A) of the cavity 725 (e.g., the array of retractable contacts 305 described with respect to FIGS. 3A and 3B). The retractable contacts 755 of the array of retractable contacts 750 may be arranged in a spatial configuration that spans one or more rows on the first internal surface 730. The retractable contacts 755 can be located in a spatial configuration such that each of the retractable contacts 755 can be aligned to correspond with contacts 760 of a respective connector 765. For example, the spatial configuration may be staggered, aligned, wavy, honeycomb, arbitrary speckled, diagonal, grid, checkerboard, circular, annular, haring bone, periodic, or a combination thereof. The spatial configuration allows the header 710 to accommodate connectors with varying numbers of electrical contacts. In some embodiments, retractable contacts 755 are integrated into the header geometry in such a way that there is a "mechanical interference" of the retractable contacts 755 in its actuated state and the connector (e.g., interference cause by mechanical pressure from an opposing set of retractable contacts or the opposing second internal surface 735). This "mechanical interference" creates the normal force to maintain the electrical connection between the retractable contacts 755 and the contacts 760 of the connector 765.

The header 710 further comprises an array of connection terminals 770 on the housing 720 or the moveable plate 715. One or more of the connection terminals 775 of the array of connection terminals 770 is electrically connected to the electronics module 705 and electrically connectable to a retractable contact 755 of the array of retractable contacts 750. In various embodiments, the connection terminals 770 are comprised of one or more layers of conductive material. The conductive material selected for the connection terminals 770 should be biocompatible, have good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A medical device comprising:
   an electronics module; and
   a header for connecting to the electronics module to a lead assembly, the header comprising:
      a housing comprising (i) a cavity having a hollow portion defined by an internal surface substantially matching an external surface of a connector of the lead assembly, and (ii) an opening in communication with the hollow portion;
      an array of retractable contacts extending through the internal surface into the hollow portion, wherein the array of retractable contacts are arranged in one or more rows; and
      an array of connection terminals on the housing, wherein each connection terminal of the array of connection terminals is: (i) electrically connected to the electronics module, and (i) electrically connectable to a retractable contact of the array of retractable contacts.

2. The medical device of claim 1, wherein the retractable contacts comprise: a body with a columnar shape, a tip with a semi-circular shape, and an actuator for driving the retractable contacts in a direction perpendicular to the internal surface.

3. The medical device of claim 1, wherein the retractable contacts comprise: a body with a spherical shape that allows the retractable contacts to rotate in a first direction parallel to the internal surface, and an actuator for driving the retractable contacts in a second direction perpendicular to the internal surface.

4. The medical device of claim 2, wherein the actuator comprises: one or more set screws, a hydraulic bladder, a pneumatic bladder, a compression spring, a leaf spring, or a combination thereof.

5. The medical device of claim 1, wherein the cavity further includes a second internal surface located on a side of the cavity that is opposite of the first internal surface.

6. A medical device comprising:
   an electronics module; and
   a header for connecting the electronics module to a lead assembly, the header comprising:
      a housing comprising (i) a cavity having a central axis, a first internal surface, and a second internal surface located on a side of the cavity that is opposite of the first internal surface, and (ii) an opening aligned with the central axis or plane of the cavity;
      an array of retractable contacts extending through the first internal surface towards the central axis or plane of the cavity, wherein retractable contacts of the array of retractable contacts are arranged in a spatial configuration that spans one or more rows on the first internal surface;
      an array of connection terminals on the second internal surface, wherein each connection terminal of the array of connection terminals is electrically connected to the electronics module; and
      a movable plate,
      wherein the first internal surface of the cavity is a surface of the movable plate; and
      wherein the header further comprises an actuator for driving the movable plate in a direction perpendicular to the central axis or plane of the cavity.

7. The medical device of claim 6, wherein the actuator comprises one or more set screws, a hydraulic bladder, a pneumatic bladder, a compression spring, a leaf spring, or a combination thereof.

8. The medical device of claim 6, wherein the array of connection terminals on the second internal surface are arranged in the same spatial configuration that spans one or more rows on the second internal surface.

9. A medical device comprising:
   an electronics module; and
   a header for connecting to the electronics module to a lead assembly, the header comprising:
      a housing comprising (i) a cavity having a central axis, a first internal surface, and a second internal surface located on a sid okay e of the cavity that is opposite of the first internal surface, wherein the first internal surface and the second internal surface substantially match an external surface of a connector of the lead assembly, and (ii) an opening aligned with the central axis or plane of the cavity;

a first array of retractable contacts extending through the first internal surface towards the central axis or plane of the cavity, wherein retractable contacts of the first array of retractable contacts are arranged in a first spatial configuration that spans one or more rows on the first internal surface;

a first array of connection terminals on the housing, wherein each connection terminal of the first array of connection terminals is: (i) electrically connected to the electronics module, and (i) electrically connectable to a retractable contact of the first array of retractable contacts;

a second array of retractable contacts extending through the second internal surface towards the central axis or plane of the cavity, wherein retractable contacts of the second array of retractable contacts are arranged in a second spatial configuration that spans one or more rows on the second internal surface; and a second array of connection terminals on the housing, wherein each connection terminal of the second array of connection terminals is: (i) electrically connected to the electronics module, and (i) electrically connectable to a retractable contact of the second array of retractable contacts.

10. The medical device of claim 9, wherein the retractable contacts of the first array of retractable contacts and the second array of retractable contacts comprise: a body with a columnar shape, a tip with a semi-circular shape, and an actuator for driving the retractable contacts in a direction perpendicular to the central axis or plane of the cavity.

11. The medical device of claim 10, wherein the actuator comprises: one or more set screws, a hydraulic bladder, a pneumatic bladder, a compression spring, a leaf spring, or a combination thereof.

12. The medical device of claim 9, wherein the retractable contacts of the first array of retractable contacts and the second array of retractable contacts comprise: a body with a spherical shape that allows the retractable contacts to rotate in a first direction parallel to the central axis or plane of the cavity, and an actuator for driving the retractable contacts in a second direction perpendicular to the central axis or plane of the cavity.

* * * * *